US011017889B1

United States Patent
Havard et al.

(10) Patent No.: US 11,017,889 B1
(45) Date of Patent: May 25, 2021

(54) METHODS AND SYSTEMS FOR GRAPHICAL MEDICINE DISPLAY

(71) Applicant: Express Scripts Strategic Development, Inc., St. Louis, MO (US)

(72) Inventors: Michael Ross Havard, Florissant, MO (US); Timothy Andrew Cox, University City, MO (US); Grant Paris Miller, Clayton, MO (US); Katherine H. Sundararaman, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 499 days.

(21) Appl. No.: 15/795,901

(22) Filed: Oct. 27, 2017

Related U.S. Application Data

(62) Division of application No. 13/338,770, filed on Dec. 28, 2011, now Pat. No. 9,852,261.

(51) Int. Cl.
*G16H 10/60* (2018.01)
*G06F 19/00* (2018.01)
(Continued)

(52) U.S. Cl.
CPC ......... *G16H 10/60* (2018.01); *G06F 19/3456* (2013.01); *G06Q 50/22* (2013.01); *G16H 20/10* (2018.01); *G16H 70/40* (2018.01)

(58) Field of Classification Search
CPC ........ G16H 10/60; G16H 15/00; G16H 20/10; G16H 40/60; G06F 19/3456; G06Q 50/22
See application file for complete search history.

(56) References Cited

U.S. PATENT DOCUMENTS

2002/0029223 A1\* 3/2002 Rice ..................... G06F 19/3456
2006/0294108 A1\* 12/2006 Adelson ................ G06Q 10/06
(Continued)

FOREIGN PATENT DOCUMENTS

WO WO-2010028288 A2 \* 3/2010 ........... C12Q 1/6886

OTHER PUBLICATIONS

Fioravanti et al., A Mobile Feedback System for Integrated E-health Platforms to improve Self-Care and Compliance of Diabetes Mellitus Patients, Sep. 3, 2011, IEEE EMBS, pp. 3550-3553. (Year: 2011).\*

(Continued)

*Primary Examiner* — Christopher L Gilligan

(57) ABSTRACT

Methods and systems for graphical medicine display are described. In one embodiment, prescription drug data associated with a prescription drug is accessed. The prescription drug is associated with a member. The prescription drug data includes prescription name data, prescription packaging data, prescription pill data, and dosage data. A prescription pill indicator and a prescription package indicator based on the prescription drug data are determined. A medicine display based on the prescription drug data associated with the prescription drug is generated. The medicine display includes the prescription pill indicator in association with the prescription package indicator, a prescription name indicator, and a dosage indicator. The prescription name data, the prescription packaging data, and the prescription pill data are associated with the prescription drug and the dosage data is associated with the member.

18 Claims, 13 Drawing Sheets

(51) Int. Cl.
*G06Q 50/22* (2018.01)
*G16H 70/40* (2018.01)
*G16H 20/10* (2018.01)

(56) References Cited

U.S. PATENT DOCUMENTS

| | | | |
|---|---|---|---|
| 2008/0056556 A1* | 3/2008 | Eller | G06F 19/3462 |
| | | | 382/142 |
| 2008/0162188 A1* | 7/2008 | Kripalani | G06Q 50/24 |
| | | | 705/3 |
| 2009/0030725 A1 | 1/2009 | Nadas | |
| 2010/0017754 A1* | 1/2010 | Cafer | G06F 3/04817 |
| | | | 715/835 |
| 2011/0184753 A1 | 7/2011 | Tripoli | |
| 2011/0275051 A1* | 11/2011 | Hanina | G06F 19/3418 |
| | | | 434/365 |
| 2013/0104077 A1 | 4/2013 | Felt | |
| 2013/0117696 A1* | 5/2013 | Robertson | G16H 20/10 |
| | | | 715/763 |
| 2013/0151572 A1* | 6/2013 | Brocato | G06F 16/213 |
| | | | 707/805 |

OTHER PUBLICATIONS

Ferranti et al., Using a computerized provider order entry system to meet the unique prescribing needs of children: description of an advanced dosing model, Feb. 21, 2011, BMC Medical Informatics and Decision Making, pp. 1-12. (Year: 2011).*

* cited by examiner

METHODS AND SYSTEMS FOR GRAPHICAL MEDICINE DISPLAY

CROSS REFERENCE TO RELATED APPLICATIONS

This application is a divisional of and claims the benefit of and priority to co-pending U.S. application Ser. No. 13/338,770, filed Dec. 28, 2011, which is incorporated herein by reference in its entirety

FIELD

The field relates to graphical displays, and more particularly to graphical display of medicines.

BACKGROUND

Patients may consume a number of prescription drugs or other medicines during the course of a day or week. These patients may keep lists or other records reminding them of how and when to consume their medicines. These patients may also refer to packaging while trying to adhere to dosage regimens for their medicines. It may be difficult for patients to keep track of all their medicines, let alone for them to remember proper dosage, refill, and other medicine and prescription information.

DETAILED DESCRIPTION

Example methods and systems for graphical medicine display are described. In the following description, for purposes of explanation, numerous specific details are set forth in order to provide a thorough understanding of example embodiments. It will be evident, however, to one of ordinary skill in the art that embodiments of the invention may be practiced without these specific details.

A patient may be a member of a pharmacy benefit manager (PBM). The PBM may store data regarding member usage of prescription drugs. This data may be leveraged in order to provide a member with a graphical medicine display available from a member's mobile phone, tablet, portable computer, personal computer, or other mobile electronic device.

In general, prescription drug and medicine data may be accessed from a PBM, for example. One or more operations may be performed on the prescription drug and medicine data to generate a graphical medicine display that may include a representation of a medicine cabinet. The generated display may be presented on a member's mobile electronic device. The medicine display may be based on the member's prescription drug and medicine data, and may be customized as desired by the member.

Figure 1:
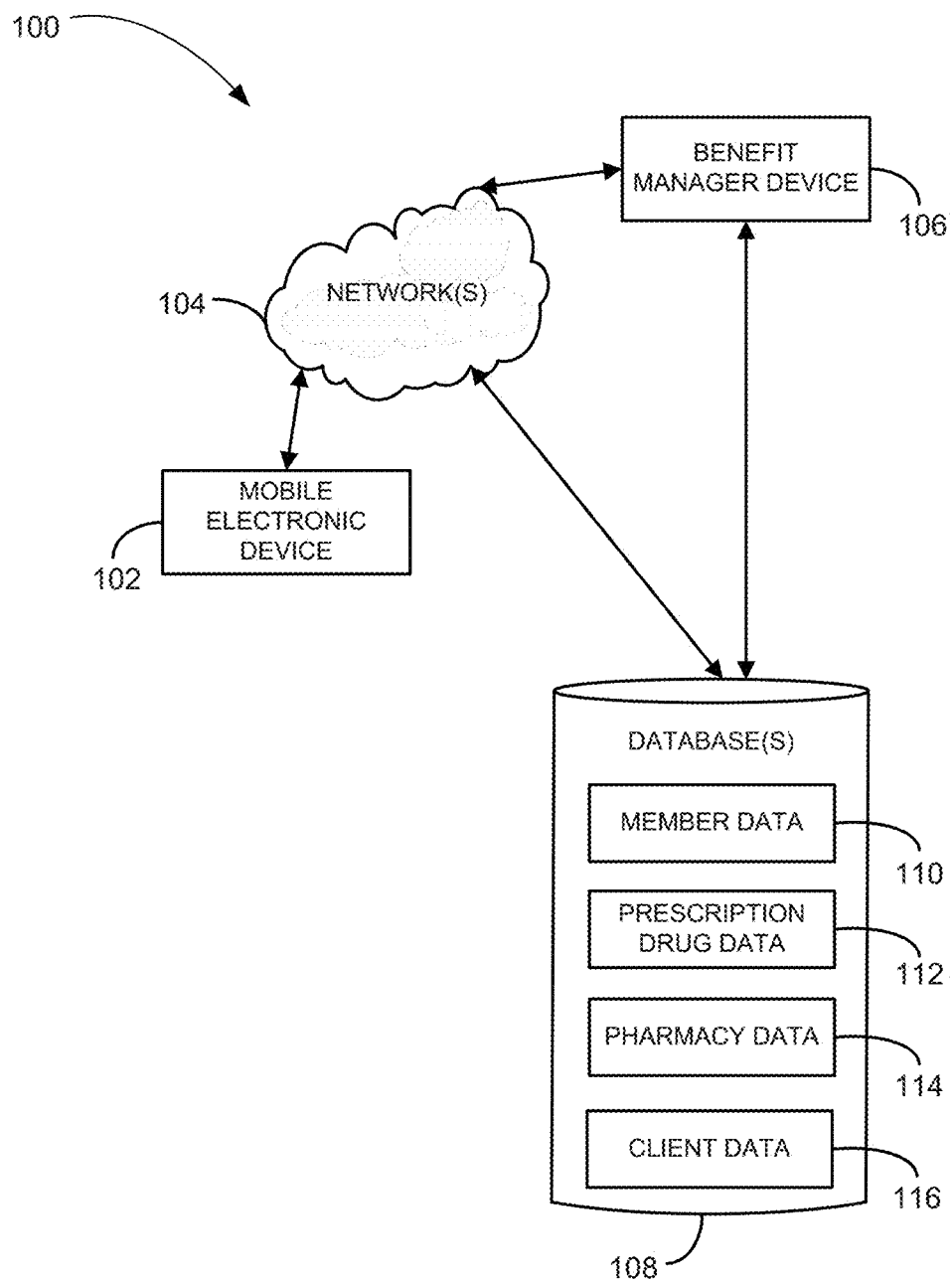
FIG. 1 is a block diagram of an example system, according to an example embodiment.

FIG. 1 is a block diagram of an example system 100, according to an example embodiment. The system 100 is an example environment in which a graphical medicine display may be generated and presented to a member. The system 100 includes a mobile electronic device 102 in communication with a benefit manager device 106 over a network 104.

The mobile electronic device 102 is used by a mobile device operator. The mobile device operator may be a member of a drug benefit plan. However, the mobile device operator may be another person operating the mobile electronic device 102 on behalf of the member. Examples of such people include parents, guardians, caregivers, and the like. In addition, non-member patients of a pharmacy may also use the mobile electronic device.

The mobile electronic device 102 may be a stand-alone device that solely provides at least some of the functionality to enable the generation and display of a graphical medicine display, or may be a multi-use device that has functionality outside of the methods and systems for generating and displaying a graphical medicine display as described herein. Examples of the mobile electronic device 102 include an IPAD or IPHONE device by Apple, Inc., mobile electronic devices powered by ANDROID by Google, Inc. a BLACKBERRY device by Research In Motion Limited, NOKIA devices, and netbook computers. Other types of mobile electronic devices may also be used. These may include, but are not limited to, tablets, portable computing devices and portable communication devices.

The network 104 by which the mobile electronic device 102 communicates with the benefit manager device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 may be a device operated by an entity at least partially responsible for prescription drug and/or medicine management of the member. While the benefit manager operating the benefit manager device 106 is typically a PBM, other entities may operate the benefit manager device 106 either on behalf of themselves, the PBM, or another entity. Examples of other entities that may operate the benefit manager device 106 include a health maintenance organization (HMO), a health insurance company, or the like. Such entities may, in some embodiments, provide a prescription drug benefit directly or through a PBM.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The amount of reimbursement paid to the pharmacy by the client and/or member may be based on the type of pharmacy network in which the pharmacy is included. Other factors may be used to determine the reimbursement amount in addition to the type of pharmacy network.

In some embodiments, a mobile application or app may be downloaded, installed, and launched on the mobile electronic device 102 to enable generation and display of a graphical medicine display. The mobile application may take advantage of hardware and/or software functionality provided by manufacturers of the mobile electronic device 102 and/or developers of the operating system of the mobile electronic device 102. For example, the mobile application may use the SAFARI web browser on the IPAD or IPHONE device, the webkit browser on an ANDROID device, or MOBILE INTERNET EXPLORER on a WINDOWS MOBILE device. The mobile application may include instructions that when executed on the mobile electronic device 102 or on the benefit manager device 106 cause a machine to change its state or perform tasks within the machine and with other machines.

The mobile electronic device 102 may be in a client-server relationship with the benefit manager device 106, a peer-to-peer relationship with the benefit manager device 106, or in a different type of relationship with the benefit manager device 106.

The benefit manager device 106 may be in communication directly (e.g., through local storage) and/or through the network 104 (e.g., in a cloud configuration or software as a service) with a database 108.

The member data 110 may include information regarding the members associated with the PBM. Examples of the member data 110 include name, address, telephone number, e-mail address, claim history, co-pay history, prescription drug history, and the like. The member data 110 may include an employer identifier that identifies the employer associated with the member and/or a member identifier that identifies the member to the employer.

The prescription drug data 112 may include, but is not limited to prescription name data, prescription packaging data, prescription pill data, dosage data and instructions, refill data, prescription drug label data, prescription drug expiration data, prescription drug adherence data, prescription drug images (e.g., image data) and photographs (e.g., photograph data), and pill images (e.g., image data) and photographs (e.g., photograph data).

One or more of the types of prescription drug data discussed herein may overlap or may be included in more than one data category. For example, the prescription drug packaging data may include information that also may be included in the prescription drug label data, or the prescription drug image data. Also for example, the prescription name data may be included in the prescription drug label data.

The pharmacy data 114 may include information regarding pharmacies associated with the PBM. These pharmacies may be retail pharmacies. Further, the client data 116 may include information regarding clients associated with the PBM, which may be, for example, employers or other organizations.

While the member data 110, the prescription drug data 112, the pharmacy data 114, and the client data 116 are shown in FIG. 1 as being separate data categories, the member data 110, the prescription drug data 112, the pharmacy data 114, and the client data 116 may overlap in the types of data that may be included in each data category. For example, some of the prescription drug data 112 may be member specific, and may be included in the member data 112.

The member data 110 and/or the prescription drug data 112 may include or reflect one, some, or all of prescribed drugs or other medicines of the member. The data may reflect current prescription drugs or other medicines, historical prescription drugs or other medicines (e.g. that are no longer being taken by the member), and/or future prescription drugs or other medicines (e.g., a prescription drug that has not yet been filled or an expired medicine that a member is likely to rebuy).

The prescription name data includes name and identification information of prescription drugs that have been prescribed to the member. Examples of the prescription name data include PRILOSEC, LIPITOR, and XANAX. Examples of identification information include a national drug code (NDC) and/or letters and numbers that may be printed on the drug packaging or on the drug itself, or a drug classification.

The prescription packaging data includes information regarding the packaging of prescription drugs that have been prescribed to the member. The prescription packaging data may include, by way of example, words appearing on a box or bottle in which the prescription drug is shipped, colors of the box, bottle, or tube holding the prescription drug, ingredient information, warning information, or manufacturer information.

The prescription pill data may include information regarding a pill of a prescription drug that has been prescribed to the member. The prescription pill data may include, by way of example, a color of the pill, size of the pill, any identification numbers or letters that may be on the pill, a potency of the pill, or a type of pill (e.g., capsule or tablet). When the prescription drug is not in the form of a pill, other similar types information may be captured (e.g., color of a liquid) as part of the prescription pill data and/or the dosage data.

The dosage data may include information regarding a dosage of a prescription drug that has been prescribed to the member. The dosage data may include, by way of example, a number of pills the member is to take, how often the member is to take the pills, or an amount (e.g., in milligrams) of the prescription drug the member is to take.

The prescription drug image data may include an image of a prescription drug that has been prescribed to the member. The image may be an image created that resembles or is what the prescription drug package or pill looks like. This image may be used when displaying a prescription drug package indicator or a prescription drug pill indicator at the mobile electronic device 102 to the member. The prescription drug image data may also include a standard image of what the prescription drug prescribed to the member is supposed to look like. The standard image may be an actual image, a similar image, or a computer generated image.

The prescription drug refill data may include a number of refills of a prescription drug that the member has left under his or her prescription. The prescription drug expiration data may include an expiration date for a prescription drug that was shipped or sold or otherwise fulfilled to the member.

The prescription label data may include data printed on a label of a prescription drug that has been prescribed to the member. The label may have been custom print for the member, and may include the member's name, type of prescription drug, dosage information, and warning information, among other information, some of which may be been described above in connection with other types of prescription drug data. The prescription label data may also include an image or photograph of the label shipped or sold with the prescription drug to the member.

The prescription drug adherence data may include data regarding the member's adherence to a treatment or dosage prescribed for the member in connection with a prescription drug. The prescription drug adherence data may include information regarding whether the member has been taking the prescription drug as instructed, has been taking the prescribed dose of the prescription drug in the prescribed timeframe, or has deviated from the prescribed treatment or dosage. The prescription drug adherence data may be received from the mobile electronic device 102 associated with the member, if the member inputs such information into the mobile electronic device 102.

The prescription drug photograph data may include a photograph of the prescription drug package or bottle taken before the prescription drug was shipped to the member. The prescription drug photograph data may include a single photograph or multiple photographs with respect to the prescription drug package. Multiple photographs may be taken from the same angle or different angles of the prescription drug package. The photographs may include, for example, photographs of the prescription drug label, top-down photographs of the open prescription drug bottle including images of the pills, or images of the pills. The prescription drug image data may also include a standard photograph of what the prescription drug or pill prescribed to the member is supposed to look like.

While the database 108 is discussed here in connection with the member data 110, the prescription drug data 112, the pharmacy data 114, and the client data 116, system 100 may include multiple databases in order to facilitate generation of a graphical medicine display. Further, each type of data described above may be stored in multiple databases and/or may each include data overlapping in multiple data categories.

Certain data from the database 110 may be stored on the mobile electronic device 102 separate from or in addition to the data stored in the database 110. In some embodiments, the data may be stored on the mobile electronic device 102 instead of in the database 110. In some embodiments, the mobile electronic device 102 is pre-loaded with certain data.

While the system 100 in FIG. 1 is shown to include single devices 102, and 106, multiple devices may be used. The devices 102 and 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102 and 106 or in parallel to link the devices 102 and 106.

Figure 2:
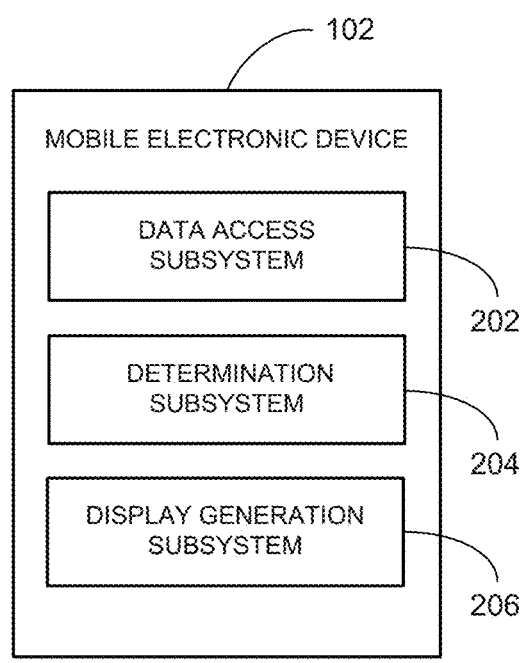
FIG. 2 is a block diagram of an example mobile electronic device that may be deployed within the system of FIG. 1, according to an example embodiment.

FIG. 2 illustrates the mobile electronic device 102, according to an example embodiment. The mobile electronic device 102 may facilitate generation and display of a graphical medicine display. The mobile electronic device 102 may be deployed in the system 100, or may otherwise be used.

The mobile electronic device 102 may include a data access subsystem 202, a determination subsystem 204, and/or a display generation subsystem 206. The data access subsystem 202, the determination subsystem 204, and the display generation subsystem 206 may interact or exchange data in order to facilitate generation and display of a graphical medicine display.

The data access subsystem 202 may enable access to data from the database 108, including the member data 110, prescription drug data 112, the pharmacy data 114, and the client data 116. The data access subsystem may access the name data, the prescription packaging data, the prescription pill data, the dosage data and instructions, the refill data, the prescription drug label data, the prescription drug expiration data, the prescription drug adherence data, the prescription drug images (e.g., image data) and photographs (e.g., photograph data), and the pill images (e.g., image data) and photographs (e.g., photograph data). The data access subsystem 202 may access the data above based on changes to the data or indicators being generated, as will be described below.

The determination subsystem 204 may enable determination of which indicators or information are to be generated or displayed in the graphical medicine display based on data accessed by the data access subsystem 202. The display generation subsystem 206 may enable generation and display of the indicators or information determined by the determination subsystem 204. Each of the subsystems 202-206 may include additional features and functionality, some of which will be described below.

Figure 3:
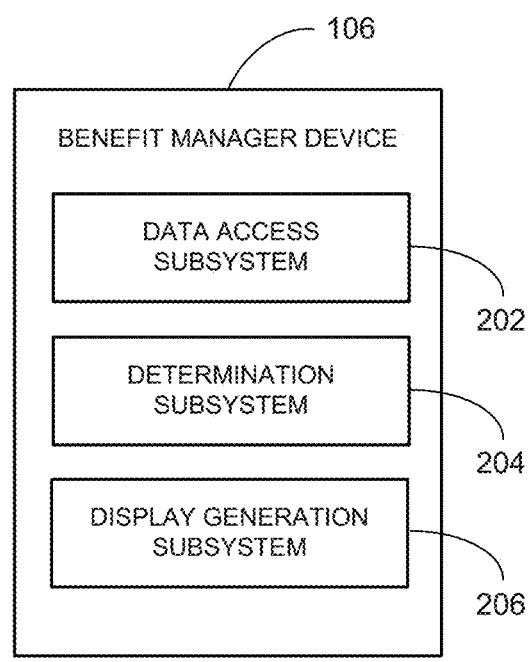
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the data access subsystem 202, the determination subsystem 204, and the display generation subsystem 206. In some embodiments, one or more of the various subsystems 202-206 when used may provide, e.g., server-side functionality to the mobile electronic device 102. By way of example, the data access subsystem 202 may be deployed in both the mobile electronic device 102 and the benefit manager device 106. The mobile electronic device 102 may then perform some of the functionality while other functionality is performed by the benefit manager device 106.

Figure 4:
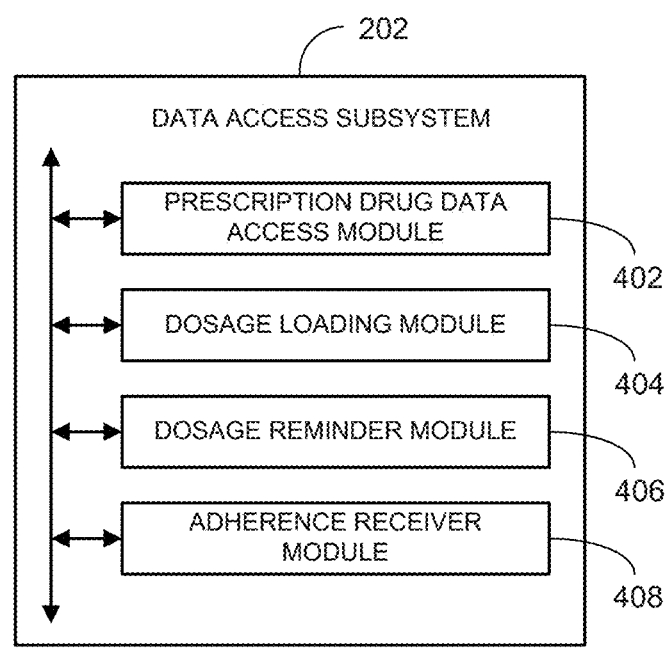
FIG. 4 is a block diagram of an example data access subsystem that may be deployed within the mobile electronic device of FIG. 2 or the benefit manager device of FIG. 3, according to an example embodiment.

FIG. 4 illustrates an example data access subsystem 202 that may be deployed in the mobile electronic device 102, the benefit manager device 106, or otherwise deployed in another system. The modules are communicatively coupled and included in the data access subsystem 202 to enable various data access functionalities. The modules of the data access subsystem 202 that may be included are a prescription drug data access module 402, a dosage loading module 404, a dosage reminder module 406, and adherence receiver module 408. Other modules may also be included.

In some embodiments, the modules of the data access subsystem 202 may be distributed so that some of the modules are deployed in the mobile electronic device 102 and some modules are deployed in the benefit manager device 106. In one embodiment, the modules are deployed in memory and executed by a processor coupled to the memory. The functionality included within the modules 402-408 may be combined into a lesser number of modules, further divided among a greater number of modules, or redistributed among existing modules. Other configurations including the functionality of the modules 402-408 may be used.

In some embodiments, prescription drug data access module 402 may access the prescription drug data 112 associated with a prescription drug or member. The prescription drug may be associated with a member. The prescription drug data 112 may be any of the prescription drug data discussed above, including, but not limited to the prescription name data, the prescription packaging data, the prescription pill data, and the dosage data. The prescription name data, the prescription packaging data, and the prescription pill data are associated with the prescription drug and the dosage data is associated with the member.

In some embodiments, the dosage loading module 404 may load or preload dosage instructions associated with a prescription drug from the dosage data in the database 108. Further, the dosage reminder module 406 may load a dosage reminder for the member prescribed the prescription drug into an electronic calendar associated with the member. A single dosage reminder or multiple dosage reminders may be loaded.

The electronic calendar may be included on the graphical medicine display. For example, the electronic calendar may be overlaid on the graphical medicine display. The electronic calendar may also be generated or rendered on an additional display, or may otherwise be displayed. The electronic calendar may be a calendar available from a general purpose calendaring and scheduling application.

Further, the adherence receiver module 408 may receive a member dose indication from the mobile electronic device 102. The member dose indication may correspond to or reflect whether the member followed or adhered to a prescription drug treatment or prescription drug dosage (e.g., a number of pills a day over a time period) associated with the prescription drug and the member. For example, if the member takes a pill in the morning according to the prescription drug dosage, the member may indicate through a user interface on the mobile electronic device 102, that the member took the pill.

Figure 5:
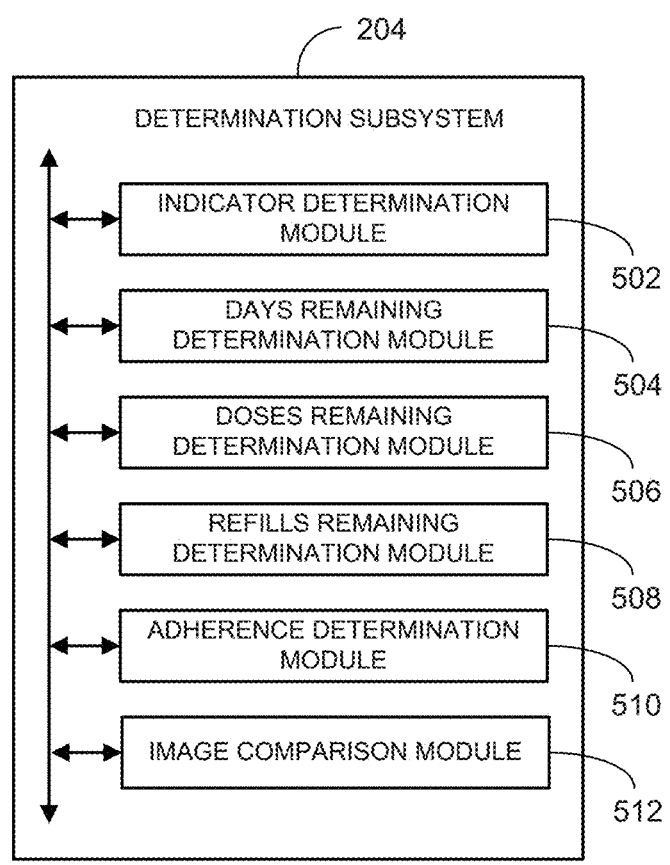
FIG. 5 is a block diagram of an example determination subsystem that may be deployed within the mobile electronic device of FIG. 2 or the benefit manager device of FIG. 3, according to an example embodiment.

FIG. 5 illustrates an example determination subsystem 204 that may be deployed in the mobile electronic device 102, the benefit manager device 106, or otherwise deployed in another system. One or more modules are communicatively coupled and included in the determination subsystem 204 to enable various determination functionalities. The modules of determination subsystem 204 that may be included are an indicator determination module 502, a days remaining determination module 504, a doses remaining determination module 506, a refills remaining determination module 508, an adherence determination module 510, and an image comparison module 512. Other modules may also be included.

In some embodiments, the modules of the determination subsystem 204 may be distributed so that some of the modules are deployed in the mobile electronic device 102 and some modules are deployed in the benefit manager device 106. In one embodiment, the modules are deployed in memory and executed by a processor coupled to the memory. The functionality included within the modules 502-512 may be combined into a lesser number of modules, further divided among a greater number of modules, or redistributed among existing modules. Other configurations including the functionality of the modules 502-512 may be used.

In some embodiments, the indicator determination module 502 may determine a prescription pill indicator and/or a prescription package indicator based on the prescription drug data 112. For example, with the packaging data, the pill data, the image data, and/or the photograph data received from the data access subsystem 202, the indicator determination module 502 may determine what image should be shown to the member in the graphical medicine display to represent a prescription drug having been prescribed to the member.

In some embodiments, the days remaining determination module 504 may determine a number of days for consuming a prescription drug remaining for the member based on the prescription drug data and the dosage data. For example, if the data access subsystem 202 accesses information from the prescription drug data 112, and dosage data represents that there are 10 pills in a prescription drug package and that the member is to consume 1 pill a day, on day 6, the days remaining determination module 504 may determine that the number of days remaining is 4 days.

In some embodiments, the doses remaining determination module 506 may determine a number of doses of the prescription drug remaining for the member based on the prescription drug data 112 and the dosage data. For example, if the data access subsystem 202 accesses information from the prescription drug data 112 and the dosage data represents that there are 20 doses in a prescription drug package and that the member is to consume 2 doses per day, after day 6, the doses remaining determination module 506 may determine that the number of doses remaining is 8 doses.

In some embodiments, the refills determination module 508 may determine a number of refills of the prescription drug remaining for the member based on the prescription drug data 112 and the dosage data. For example, if the data access subsystem 202 accesses information from the prescription drug data 112 and the dosage data represents that there are 5 refills in a prescription and that the member has been shipped 2 refills, the refills remaining determination module 508 may determine that the number of refills remaining is 3 refills.

Further, the adherence determination module 510 may determine an adherence metric based on the prescription drug data 112 associated with the prescription drug and the member dose indication described above that may be received via the adherence receiver module 408. For example, if the member dose indication represents that the member properly took 9 out of 10 doses of the prescription drug, the adherence determination module 510 may determine that the adherence metric for the member is 90%.

Additionally, the image comparison module 512 may compare a prescription drug image associated with the prescription drug to a standard prescription drug image associated with the prescription drug. For example, a PBM may take a photograph or keep an image of each prescription drug package sent to a member, which may be stored with the image data or the photograph data. The PBM may also have a standard prescription drug image of the prescription drug that may be stored with the image data or the photograph data. The image comparison module 512 may compare the photograph or image of the prescription drug sent to the member with the standard prescription drug image in order to determine whether the proper prescription drug was sent to the member according to the prescription.

Figure 6:
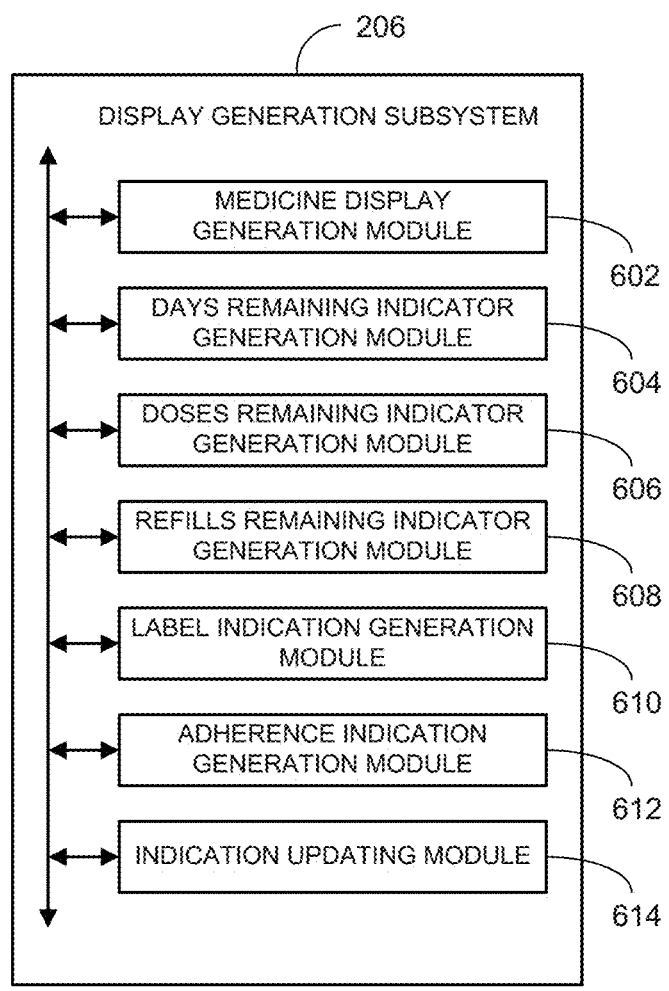
FIG. 6 is a block diagram of an example display generation subsystem that may be deployed within the mobile electronic device of FIG. 2 or the benefit manager device of FIG. 3, according to an example embodiment.

FIG. 6 illustrates an example display generation subsystem 206 that may be deployed in the mobile electronic device 102, the benefit manager device 106, or otherwise deployed in another system. One or more modules are communicatively coupled and included in the display generation subsystem 206 to enable various display generation related functionalities. The modules of the display generation subsystem 206 that may be included are a medicine display generation module 602, a days remaining indicator generation module 604, a doses remaining indicator generation module 606, a refills remaining indicator generation module 608, a label indication generation module 610, an adherence indication generation module 612, and an indication updating module 614. Other modules may also be included.

In some embodiments, the modules of the display generation subsystem 206 may be distributed so that some of the modules are deployed in the mobile electronic device 102 and some modules are deployed in the benefit manager device 106. In one embodiment, the modules are deployed in memory and executed by a processor coupled to the memory. The functionality included within the modules 602-614 may be combined into a lesser number of modules, further divided among a greater number of modules, or redistributed among existing modules. Other configurations including the functionality of the modules 602-614 may be used.

In some embodiments, the medicine display generation module 602 may generate a graphical medicine display (e.g., a mobile medicine cabinet) based on the prescription drug data 112 associated with the prescription drug. The medicine display may include a prescription pill indicator in association with a prescription package indicator. The prescription pill indicator and the prescription package indicator may be based on the prescription drug data 112. The medicine display may also include a prescription name indicator based on the prescription name data and a dosage indicator based on the dosage data.

The indicators described herein may be generated as part of the graphical medicine display, separate from the graphical medicine display, added to the graphical medicine display, or may otherwise be generated. The indicators described herein may also be rendered.

In some embodiments, the days remaining indicator generation module 604 may generate a days remaining indicator. The days remaining indicator may be included in the medicine display and may correspond to or reflect the number of days for consuming the prescription drug remaining for the member, as may be determined by the days remaining determination module 504.

Further, the doses remaining indicator generation module 606 may generate a doses remaining indicator. The doses remaining indicator may be included in the medicine display and may correspond to or reflect a number of doses of the prescription drug remaining for the member, as may be determined by the doses remaining determination module 506.

Also, the refills remaining indicator generation module 608 may generate a refills remaining indicator. The refills remaining indicator may be included in the medicine display and may correspond to or reflect a number of refills of the prescription drug remaining for the member, as may be determined by the refills remaining determination module 508.

In some embodiments, the label indication generation module 610 may generate a prescription drug label indicator. The prescription drug label indicator may be included in the medicine display and may be based on the prescription drug label data. The prescription drug label data may be associated with the prescription drug and the member, and may be accessed via the prescription drug data access module 402. The prescription drug label indicator may also be based on the image data and the photograph data.

In some embodiments, the adherence indication generation module 612 may generate a prescription drug adherence indicator. The prescription drug adherence indicator may be included in the medicine display and may be based on the prescription drug adherence metric described above.

In some embodiments, the indication updating module 614 may update the prescription package indicator in the medicine display. The update of the prescription package indicator may be based on an indication that the prescription packaging data changed. For example, a manufacturer may change a prescription drug package style or prescription drug bottle style. The change may be stored in the prescription drug packaging data. An indication that the prescription drug packaging data changed may be accessed via the prescription drug data access module 402.

Further, the indication updating module 614 may update the prescription drug label indicator in the medicine display. The update of the prescription drug label indicator may be based on an indication that the prescription drug label data changed. For example, a manufacturer may change a prescription drug label warning or color. The change may be stored in the prescription drug label data. An indication that the prescription drug label data changed may be accessed via the prescription drug data access module 402.

Updating the prescription drug package indicator and/or the prescription drug label indicator in the medicine display may include generating a new medicine display to reflect that data (e.g., prescription packaging data and/or prescription drug label data) has changed, as described above. Further, accessing the indication that the data (e.g., prescription packaging data and/or prescription drug label data) has changed may be based on or may include comparing new data to old data to determine that there is a change.

The display generation subsystem 206 and one or more of the modules 602-614 may generate a medicine display showing one or more of the indicators described above. In general, the display or screen is a computer generated image or series of images capable of being viewed by a person when presented on a device. The display is generally graphically rendered and presented to a device operator on a display device unit (e.g., a television screen, a computer monitor, or a mobile electronic device display) of the device.

Figure 7:
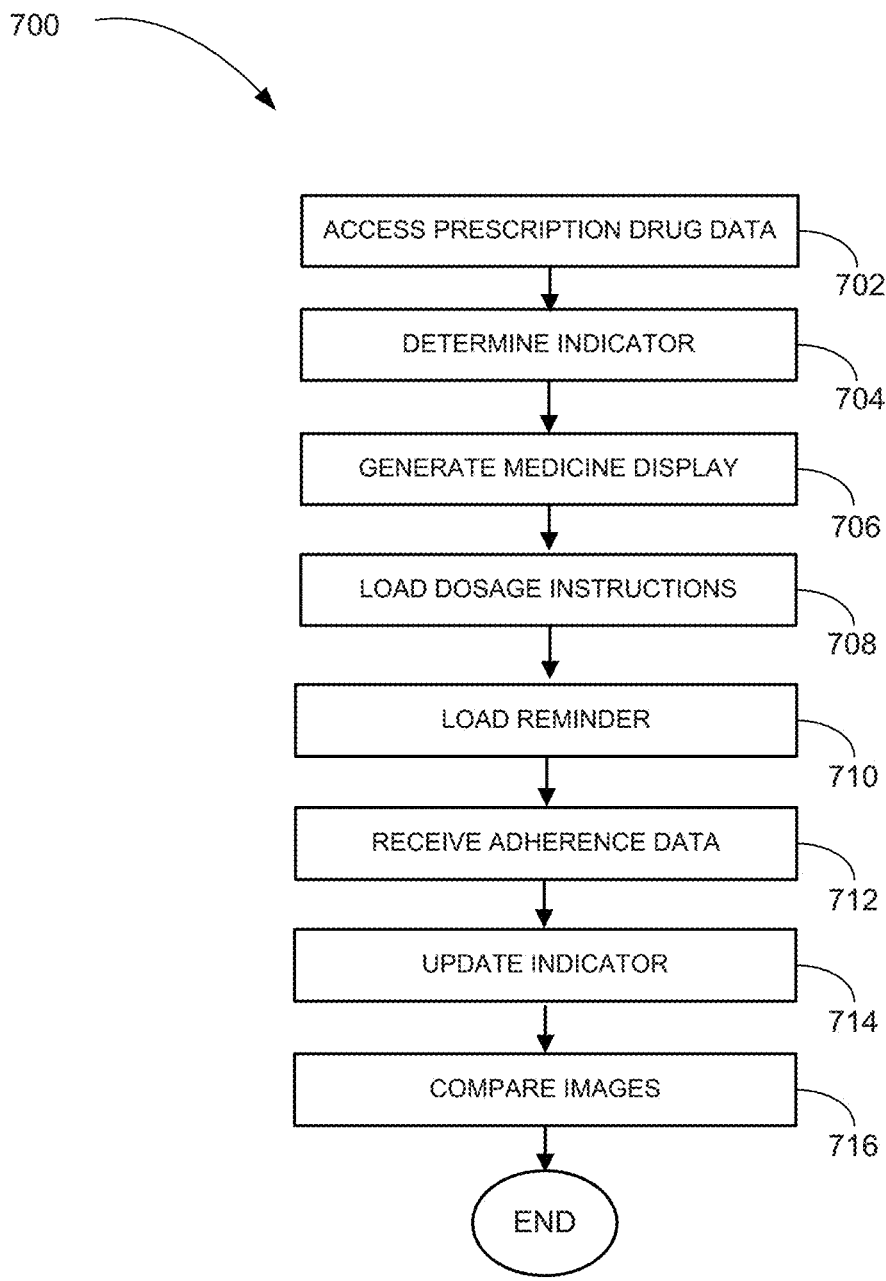
FIG. 7 is an example process flow illustrating a method for a generating and displaying a graphical medicine display, according to an example embodiment.

FIG. 7 illustrates a method 700 for enabling generation and display of a graphical medicine display according to an example embodiment. The method 700 may be performed by the mobile electronic device 102, the benefit manager device 106, partially by the mobile electronic device 102 and partially by the benefit manager device 106, or may be otherwise performed.

The prescription drug data 112 may be accessed at block 702. The prescription drug data accessed at block 702 may be any of the prescription drug data discussed herein. For example, the prescription drug data accessed may be the prescription name data, the prescription packaging data, or the prescription expiration data, any of which may be associated with a prescription drug and a member.

Single or multiple prescription drug related indicators (some of which have been described above) may be determined at block 704. For example, a prescription label indicator and a prescription package indicator may be determined. The prescription label indicator may be based on a photograph (e.g., from the photograph data) of the prescription drug before a prescription drug order was shipped or otherwise fulfilled to the member. Further, the prescription package indicator may be based on a photograph (e.g., from the photograph data) of the prescription drug before a prescription drug order was shipped or otherwise fulfilled to the member.

A medicine display may be generated at block 706. The medicine display may be a mobile medicine cabinet and may include a prescription pill indicator, a prescription package indicator, or a prescription drug expiration indicator. In some embodiments, the prescription package indicator may be based on a comparison of a prescription drug image associated with the prescription drug data 112 and a standard prescription drug image associated with the prescription drug. In this manner, it may be verified that the member was shipped the correct prescription drug.

In some embodiments, the medicine display may include a prescription drug dose reminder. The prescription drug dose reminder may indicate that the member is to follow a prescription drug treatment or prescription drug dosage associated with the prescription and the member. The prescription drug dose reminder may be based on prescription drug data 112 and the dosage data.

In some embodiments, dosage instructions may be loaded or preloaded to, e.g., the mobile electronic device 102 at block 708. The dosage instructions may be loaded or preloaded for the member associated with the prescription drug based on the dosage data associated with the member.

In some embodiments, a plurality of dose reminders may be loaded into an electronic calendar at block 710. The electronic calendar may be accessed, e.g., via the mobile electronic device 102. The plurality of dose reminders may be for the member associated with the prescription drug and may be loaded into an electronic calendar associated with the member.

In some embodiments, adherence data may be received at block 712. For example, a member dose indication may be received. The member dose indication may correspond to or reflect whether the member followed the prescription drug treatment or prescription drug dosage associated with the prescription drug and the member. The member dose indication may be received via, e.g., the mobile electronic device 102.

Further, one or more of the indicators described herein may be updated at block 714. For example, the prescription package indicator included in the medicine display may be updated, or the medicine display itself may be regenerated, based on an indication that prescription packaging data changed. Further, the prescription drug label indicator included in the medicine display may be updated based on an indication that the prescription drug label data changed.

Additionally, images may be compared at block 716. For example, a prescription drug image associated with the prescription drug data 112 may be compared with a standard prescription drug image associated with the prescription drug to determine if there is a drug match. In some embodiments, the prescription package indicator included in the medicine display may be based on the comparison of the prescription drug image associated with the prescription drug data 112 and the standard prescription drug image associated with the prescription drug if, for example, there is a drug match.

Figure 8:
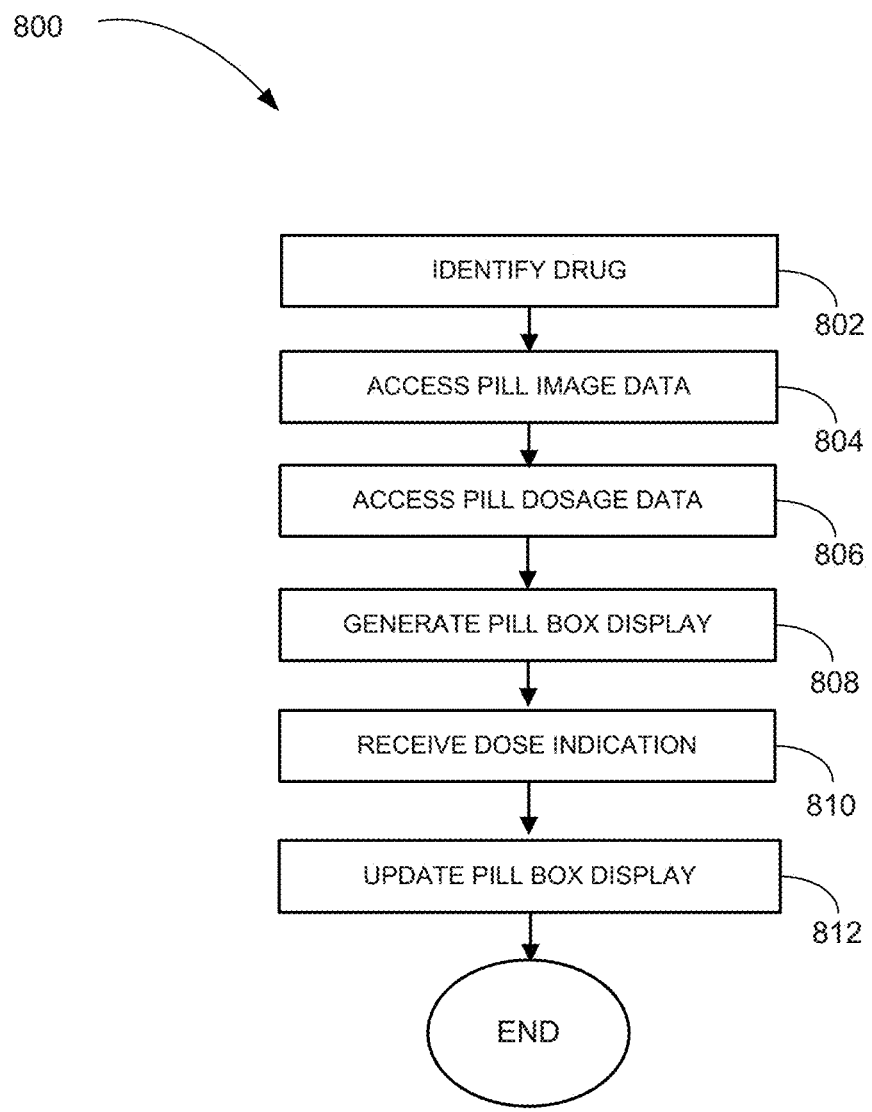
FIG. 8 is an example process flow illustrating a method for a generating and displaying a pill box display, according to an example embodiment.

FIG. 8 illustrates a method 800 for enabling generation and display of a pill box display according to an example embodiment. The method 800 may be performed by the mobile electronic device 102, the benefit manager device 106, partially by the mobile electronic device 102 and partially by the benefit manager device 106, or may be otherwise performed.

A first drug and/or a second drug may be identified at block 802. The first drug and/or second drug may be identified by determining that they are associated with a member based on member data 110 and/or prescription drug data 112.

Pill image data may be accessed at block 804. The pill image data may be associated with a number of drugs including the first drug and/or the second drug. The drugs may be associated with a member. The pill image data may include image data corresponding to each of the drugs associated with the member.

Pill dosage data may be accessed at block 806. The pill dosage data may be associated with drugs including the first drug and/or the second drug. The pill dosage data may include the dosage data (e.g., as described above) corresponding to each of the drugs associated with the member.

A pill box display may be generated at block 808. The pill box display may be based on the pill image data and the pill dosage data. The pill box display may include pill image indicators corresponding to the drugs, including the first drug and the second drug.

In some embodiments, a member dose indication may be received at block 810. The member dose indication may correspond to or reflect whether the member followed a pill dosage associated with the first drug and/or the second drug. The pill dosage may be based on the pill dosage data. For example, the member dose indication may be received via, e.g., the mobile electronic device 102. The member may input the member dose indication via, e.g., the mobile electronic device 102, to indicate that a dose of the medicine was properly taken.

In some embodiments, the pill box display may be updated at block 812. The pill box display may be updated based on the member dose indication. In some embodiments, the first drug and/or the second drug may be prescription drugs.

In some embodiments, a drug adherence metric may be determined. The drug adherence metric may be based on the pill dosage data and the member dose indication. For example, if the member was directed to take 4 pills a day, but only indicated (e.g., via the mobile electronic device 102) that 1 pill was taken for a day, it may be determined that the drug adherence metric is 25% for the member for that day.

Figure 9:
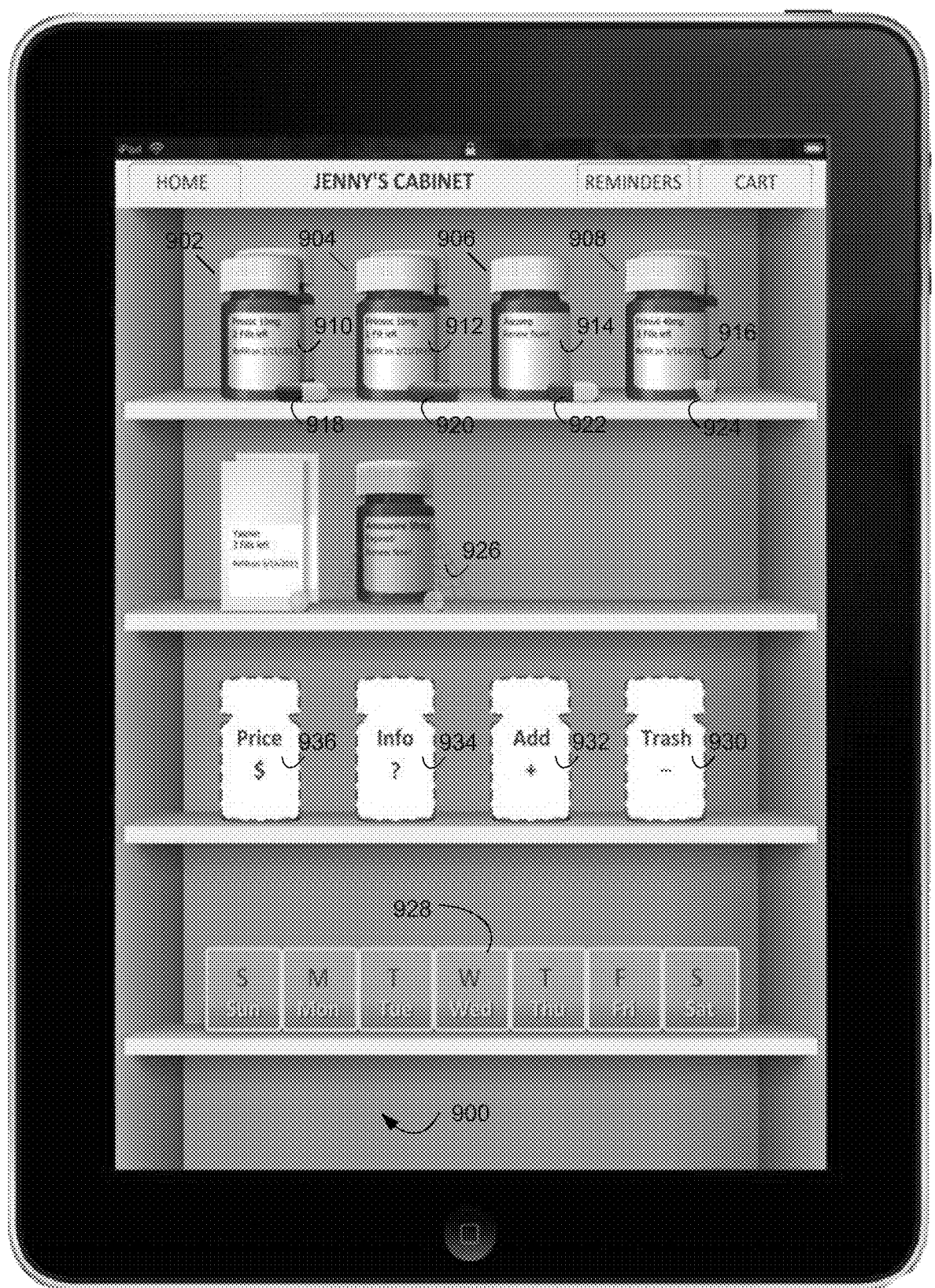
FIGS. 9-12 are example displays, according to example embodiments.

FIG. 9 illustrates an example medicine display 900 in accordance with an example embodiment. The medicine display 900 may be displayed on the mobile electronic device 102 (e.g., a tablet device) and shows an example of a medicine display that may be generated in accordance with an embodiment. For illustrative purposes only, the medicine display 900 is shown as being presented on a particular type of mobile electronic device.

The medicine display may be a mobile medicine cabinet and may be accessible by the member whenever the member has access to the tablet. The medicine display may include, as discussed above, a number of prescription package indicators (e.g., prescription package indicators 902, 904, 906, 908). The prescription package indicators may show, e.g., a bottle that the prescription drug may be shipped in.

Further, the medicine display 900 may include a prescription drug label indicator (e.g., prescription drug label indicators 910, 912, 914, 916) for each prescription drug, as described above. The medicine display 900 may additionally include a prescription pill indicator (e.g., prescription pill indicators 918, 920, 922, 924) for each prescription drug, as described above. Additionally, the medicine display 900 may include a prescription expiration indicator 926, as described above. The prescription expiration indicator 926 may be depicted as, e.g., cob webs, to indicate that the corresponding prescription has expired.

In some embodiments, the medicine display 900 may include a pill box display (e.g., pill box 928), as discussed above. The pill box display 928 may also be shown on its own, in some implementations, without the medicine display.

In some embodiments, the medicine display 900 may allow the user to organize the medicine display 900 by dragging and dropping the prescription drug package indicators (e.g., prescription package indicators 902, 904, 906, 908 of FIG. 9) to different rows or arrangements. The member may organize the medicine display 900 based on frequency of dose, therapy, or color. Further, the member may drag and drop the prescription drug package to the trash package 930 in order to dispose of it.

Similarly, the member may drag and drop the prescription drug package to the add package 932 to purchase (renew, refill, etc.) more of the prescription drug. The member may drag and drop the prescription drug package to the info package 934 to receive information about the prescription drug. The member may additionally drag and drop the prescription drug package to the price package 936 to find a price for the prescription drug.

Figure 10:
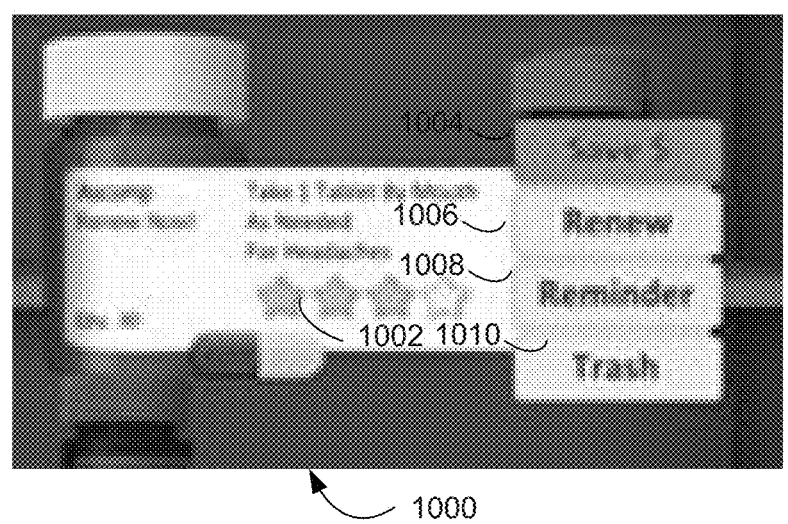

FIG. 10 illustrates an example popup display 1000 that may be generated in response to receiving a selection of a prescription drug package from the medicine display 900 of FIG. 9. In some embodiments, and as described above, the medicine display 900 may be used to collect member usage and adherence data. For example, the member may rate one or more prescription drugs through the medicine display 900 and the ratings may be aggregated and provided to prescribers. The ratings (e.g., ratings 1002) may provide the prescribers with more information about member preference and quality issues. Further, popup display 1000 may provide buttons 1004, 1006, 1008, and 1010, respectively, which, if selected, may, in response, allow the member to learn how to save money on the prescription drug, renew the prescription drug, receive a reminder regarding the prescription drug, or dispose of (trash) the prescription drug from the medicine display 900, respectively.

As discussed above, a number of reminders may be provided to members to remind them to take their prescription drugs. The reminders may be provided by email, text, device specific messaging, or by a reminder indicator on the medicine display 900. For example, if a member needs to take a dose of a prescription drug, the cap of the prescription drug image in the medicine display may glow or change color in order to alert the member to take the prescription drug dose.

In some embodiments, the member may interact with the reminder to provide feedback. For example, the member may interact with the medicine display 900 to skip a dosage, snooze the reminder, or confirm that the dosage was taken (e.g., adherence). Data received from this member feedback can be stored with, e.g., the prescription drug data 112 and can be used for reporting adherence trends, identifying variances, and sending feedback to member incentive programs.

Figure 11:

FIG. 11 illustrates an example medicine display 1100 in accordance with an example embodiment. The medicine display 1100 may be displayed on the mobile electronic device 102 and shows an example of a medicine display in accordance with an embodiment. The medicine display 1100 may be rendered on a smart phone and may provide all of the same functionality as described above with respect to the medicine display 900.

Figure 12:
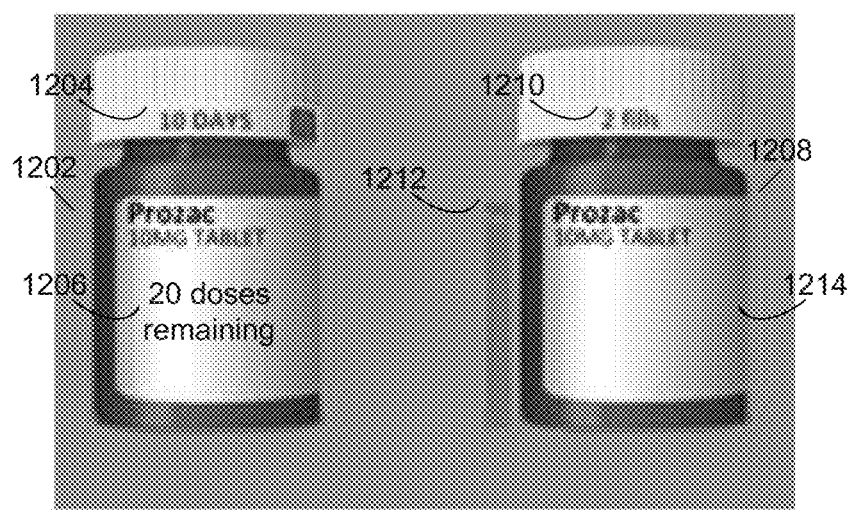

FIG. 12 illustrates example prescription drug package indicators that may be displayed in the medicine displays 900 or 1100 in accordance with an example embodiment. As discussed above, a days remaining indicator, doses remaining indicator, refills remaining indicator, prescription drug adherence indicator, and/or prescription drug dose reminder may be provided in the medicine display 900.

For example, the prescription drug package indicator 1202 may include the days remaining indicator 1204. The days remaining indicator 1204 may indicate that the member has 10 days worth of the prescription drug remaining. Further, the prescription drug package indicator 1202 may include the doses remaining indicator 1206, which may indicate that the member has 20 doses remaining.

Additionally, the prescription drug package indicator 1208 may include the refills remaining indicator 1210. The refills remaining indicator 1210 may indicate that the member has 2 refills of the prescription drug left. Also, the prescription drug package indicator 1208 may include the doses remaining indicator 1212, which may indicate that the member has 90 doses remaining. In some embodiments, the prescription drug package indicator 1208 may include the prescription drug dose reminder 1214. The prescription drug dose reminder 1214 may remind the member to take a dose of the prescription drug.

In some embodiments, synergies may be created between various types of data received through the medicine display. For example, member adherence data, lab data, and clinical data may be connected and may be used to provide the member with enhanced health care service. Through the medicine display, the member may connect with the PBM, doctor, caregiver, or pharmaceutical manufacturer to provide feedback and receive enhanced care. The member data collected may be used to identify prescription drug adherence problems, identify potential conversion opportunities, or shape client formularies. The members that actively use reminders, report usage, and adhere to therapy could receive lower copays while non-adhering members might be placed into more constrained plans, step therapy, or prior authorization to encourage therapy adherence.

In some embodiments, regular reports may be provided to the member to highlight how well they are doing, yearly savings, or health goals. For example feedback through the medicine display may be tied in with clinical and lab reporting to show how adherence may affect outcomes, such as lower cholesterol or blood pressure improvement.

While a number of different types of user interface elements have been reflected above, other types of user interface elements may be used to represent different display elements.

Figure 13:
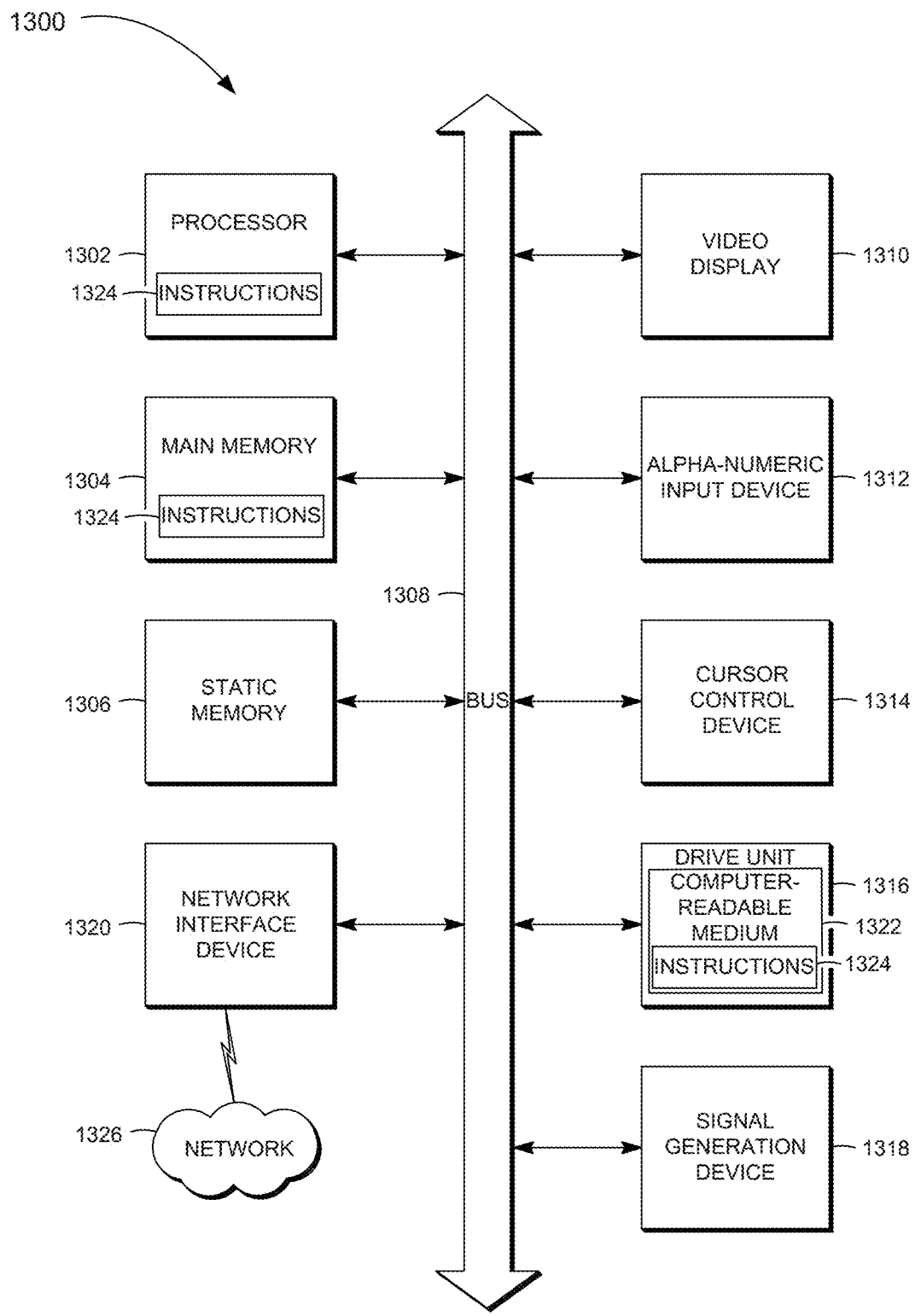
FIG. 13 is a block diagram of a machine in the example form of a computer system within which a set of instructions for causing the machine to perform any one or more of the methodologies discussed herein may be executed or stored.

FIG. 13 shows a block diagram of a machine in the example form of a computer system 1300 within which a set of instructions may be executed causing the machine to perform any one or more of the methods, processes, operations, or methodologies discussed herein. The mobile electronic device 102 or the benefit manager device 106 may include the functionality of the one or more computer systems 1300.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1300 includes a processor 1302 (e.g., a central processing unit (CPU) a graphics processing unit (GPU) or both), a main memory 1304 and a static memory 1306, which communicate with each other via a bus 1308. The computer system 1300 further includes a video display unit 1310 (e.g., a liquid crystal display (LCD) or a cathode ray tube (CRT)). The computer system 1300 also includes an alphanumeric input device 1312 (e.g., a keyboard), a cursor control device 1314 (e.g., a mouse), a drive unit 1316, a signal generation device 1318 (e.g., a speaker) and a network interface device 1320.

The drive unit 1313 includes a computer-readable medium 1322 on which is stored one or more sets of instructions (e.g., software 1324) embodying any one or more of the methodologies or functions described herein. The software 1324 may also reside, completely or at least partially, within the main memory 1304 and/or within the processor 1302 during execution thereof by the computer system 1300, the main memory 1304 and the processor 1312 also constituting computer-readable media.

The software 1324 may further be transmitted or received over a network 1326 via the network interface device 1320.

While the computer-readable medium 1322 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The terms "based upon", "based on", "at least in part", or "including" as used herein, may reflect an open-ended term or function that can reflect other elements or functions beyond those that may be explicitly recited.

The terms "a", "an", or "the", as used herein, may reflect either a single element or multiple elements when one of the terms precedes an element of the methods or systems described herein.

While the methods and systems described herein generally reflect interfacing with a member of a prescription drug plan, the methods and systems may also interface with a member of a health plan, a non-member patient of a pharmacy, or the like. The methods and systems may also interface with other types of persons.

While the methods and systems described herein generally reflect the use of a mobile electronic device, other types of devices including non-mobile electronic devices may be used.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, prescription drug data associated with a prescription drug may be accessed. The prescription drug may be associated with a member. The prescription drug data may include prescription name data, prescription packaging data, prescription pill data, and dosage data. A prescription pill indicator and a prescription package indicator may be determined based on the prescription drug data. A medicine display may be generated based on the prescription drug data associated with the prescription drug. The medicine display may include the prescription pill indicator in association with the prescription package indicator, a prescription name indicator, and a dosage indicator.

The prescription name data, the prescription packaging data, and the prescription pill data may be associated with the prescription drug and the dosage data may be associated with the member.

In an example embodiment, a first drug and a second drug may be identified. The first drug and the second drug may be associated with a member. Pill image data associated with the first drug and the second drug may be accessed. Pill dosage data associated with the first drug and the second drug may also be accessed. Further, a pill box display may be generated based on the pill image data and the pill dosage data. The pill box display may include a first pill image indicator corresponding to the first drug. The pill box display may also include a second pill image indicator corresponding to the second drug.

Thus, methods and systems for graphical medicine display have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A method comprising:
   identifying, on a processor, a first drug and a second drug associated with a member;
   accessing, on the processor, pill image data associated with the first drug and the second drug;
   accessing, on the processor, pill dosage data associated with the first drug and the second drug;
   generating, on the processor, a pill box image based on the pill image data and the pill dosage data, the pill box image including a first pill image indicator corresponding to the first drug and a second pill image indicator corresponding to the second drug, wherein generating the pill box image includes generating an interactive compliance popup graphical user interface in response to a member selecting at least one of the first pill image indicator and the second pill image indicator, wherein the interactive compliance popup graphical user interface is displayed proximately to the selected pill image indicator and is further configured to provide information to a member and to receive input on member dosing compliance from the member;
   receiving a member dose indication, wherein the member dose indication is input by the member through the interactive compliance popup graphical user interface, the member dose indication corresponding to whether the member followed a pill dosage associated with at least one of the first drug and the second drug, the pill dosage being based on the pill dosage data; and
   updating the pill box image based on the member dose indication.

2. The method of claim 1, wherein at least one of the first drug and the second drug is a prescription drug.

3. The method of claim 1, wherein generating the pill box image includes generating a collection popup graphical user interface to collect ratings data from a pharmacy benefit plan member through the pill box image by presenting a ratings popup sub-image with selectable items on top of the pill box image and reporting the collected ratings data to a prescriber device.

4. The method of claim 3, wherein receiving a member dose indication includes using the member dose indication to produce a prescription drug adherence indicator.

5. The method of claim 1, wherein generating the pill box image includes generating a ratings popup graphical user interface to collect ratings data from a pharmacy benefit plan member through the ratings popup graphical user interface by presenting a ratings popup sub-display with selectable items on top of the pill box image and reporting the collected ratings data to a prescriber device.

6. The method of claim 1, wherein generating the pill box image includes generating a full medicine image and a mobile device image, the mobile device image showing a full image of a single prescribed drug including the prescription pill indicator, a prescription package indicator, a prescription name indicator, and a dosage indicator, and the full medicine image including a plurality of prescribed drugs and action indicators including an add indictor, a trash indicator and a price indicator.

7. The method of claim 1, further comprising generating a medicine display, wherein generating the medicine display further comprises generating both an image of a prescription bottle and an image of a pill contained in the prescription bottle.

8. A method comprising:
   identifying, on a processor, a first drug and a second drug associated with a member;
   accessing, on the processor, pill image data associated with the first drug and the second drug;
   accessing, on the processor, pill dosage data associated with the first drug and the second drug;
   generating, on the processor, a pill box graphical image based on the pill image data and the pill dosage data, the pill box graphical image including a first pill image indicator corresponding to the first drug and a second pill image indicator corresponding to the second drug;
   accessing on a processor a medicine display comprising a plurality of prescription drug packages;
   generating a first interactive popup graphical user interface to collect ratings data from a pharmacy benefit plan member through the pill box graphical image by presenting a ratings popup sub-display with selectable items on top of the medicine display;
   generating a second interactive popup display to collect prescription renewal information from the member through the pill box graphical image;

receiving a member dose indication, using an interactive compliance popup graphical user interface, wherein the interactive compliance popup graphical user interface is generated in response to a member selecting at least one of the first pill image indicator and the second pill image indicator, wherein the interactive compliance popup graphical user interface is further is displayed proximately to the selected pill image indicator and is further configured to provide information to a member and to receive input on member dosing compliance from the member, the member dose indication corresponding to whether the member followed a pill dosage associated with at least one of the first drug and the second drug, the pill dosage being based on the pill dosage data; and updating the pill box graphical image based on the member dose indication.

9. The method of claim 8, wherein generating the pill box graphical image includes generating a first doses remaining indicator on the first pill image indicator and a second doses remaining indicator on the second pill image indicator.

10. The method of claim 8, wherein accessing the pill image data includes accessing multiple photographs of a prescription drug package and selecting one of the multiple photographs for use in the pill box graphical image.

11. The method of claim 10, wherein accessing multiple photographs of a prescription drug package include an image of an actual prescription drug package associated with a prescription of a member before the actual prescription drug package was delivered from a pharmacy to the member.

12. The method of claim 8, further comprising generating a third popup display to receive input on member dosing compliance.

13. The method of claim 12, wherein generating the pill box graphical image includes generating an add package icon as a drag on drop location for the first pill image indicator and the second pill image indicator to trigger at least one of the first popup display, the second popup display and the third popup display.

14. The method of claim 8, wherein generating the pill box graphical image includes generating a weekly pill box drug image.

15. A method comprising:
identifying, on a processor, a first drug and a second drug associated with a member;
accessing, on the processor, a first pill image and first pill container associated with the first drug;
accessing, on the processor, a second pill image and second pill container associated with the second drug;
accessing, on the processor, pill dosage data associated with the first drug and the second drug;
generating, on the processor, a pill box graphical image based on the pill image data and the pill dosage data, the pill box graphical image including a first pill image indicator corresponding to the first drug and a second pill image indicator corresponding to the second drug, wherein the pill image indicator includes a first state and a second state to indicate that the member should take the prescription drug associated with the member with the first state not indicating that a pill is due to be taken by the member and the second state indicating that a pill is due to be taken, wherein generating the pill box graphical image includes generating an interactive popup on the pill box graphical image in response to a member selecting at least one of the first pill image indicator and the second pill image indicator, wherein the interactive compliance popup graphical user interface is displayed proximately to the selected pill image indicator and is further configured to provide information to a member and to receive input on member dosing compliance from the member;
receiving a member dose indication, wherein the member dose indication is input by the member through the interactive compliance popup, the member dose indication corresponding to whether the member followed a pill dosage associated with at least one of the first drug and the second drug, the pill dosage being based on the pill dosage data; and
updating the pill box graphical image based on the member dose indication.

16. The method of claim 15, wherein generating the pill box pill box graphical image includes generating a popup to collect ratings data from a pharmacy benefit plan member through the pill box pill box graphical image by presenting a ratings popup sub-image with selectable items on top of the pill box graphical image and reporting the collected ratings data to a prescriber device.

17. The method of claim 16, wherein receiving a member dose indication includes using the dose indication to produce a prescription drug adherence indicator.

18. The method of claim 15, wherein the second state include a color change relative to the first state.

* * * * *